(12) United States Patent
Lodri et al.

(10) Patent No.: US 6,210,959 B1
(45) Date of Patent: Apr. 3, 2001

(54) APPARATUS FOR THE CULTIVATION AND CONCENTRATION OF NON-ADHERENT CELLS AS WELL AS FOR CO-CULTIVATION OF TWO DIFFERENT CELL SPECIES

(75) Inventors: Antal Lodri, München; Jean-Pierre Kremer, Langgeringen; Gilbert Reisbach, München, all of (DE); Guoquing Liu, Chongquing (CN)

(73) Assignee: GSF-Forschungszentrum für Umwelt und Gesundheit GmbH, Oberschleibheim (DE)

( * ) Notice: Subject to any disclaimer, the term of this patent is extended or adjusted under 35 U.S.C. 154(b) by 0 days.

(21) Appl. No.: 09/323,678

(22) Filed: Jun. 2, 1999

(30) Foreign Application Priority Data

Sep. 25, 1998 (DE) ................................ 198 44 154

(51) Int. Cl.⁷ ..................................... C12M 1/12
(52) U.S. Cl. .................. 435/297.5; 435/304.2; 435/304.3; 435/308.1; 210/296
(58) Field of Search .............. 435/297.5, 299.2, 435/304.2, 304.3, 308.1; 210/767, 296

(56) References Cited

U.S. PATENT DOCUMENTS 5,527,705 * 6/1996 Mussi et al. .................. 435/297.1
5,763,275 * 6/1998 Nagels et al. .................. 435/373

FOREIGN PATENT DOCUMENTS

| 26 27 245 C2 | 12/1976 | (DE) . |
| 8-070847 | 3/1996 | (JP) . |
| WO 93/10211 A1 | 5/1993 | (WO) . |

* cited by examiner

Primary Examiner—David A. Redding
(74) Attorney, Agent, or Firm—Sughrue, Mion, Zinn, Macpeak & Seas, PLLC

(57) ABSTRACT

For avoidance of cell aggregation and damage to the cells as well as for a reduction of the risk of contamination, an apparatus for the cultivation and concentration of non-adherent cells as well as for the co-culture of two different cell species consists of an elongate hollow vessel comprising a resting surface extending in parallel with the longitudinal axis of said vessel for positioning the hollow vessel for cell culture operation, a standing surface provided orthogonally on the longitudinal axis for positioning the hollow vessel for cell-harvesting operation or for the co-culture of two cell species, at least one closable charging and discharging opening formed on the hollow vessel on the section of the latter which is opposite to said standing surface, and a partitioning wall extending inside the hollow vessel from the standing surface thereof, which partly subdivides the interior space of the vessel, with this partitioning wall being formed at least in parts with a liquid-permeable, however cell-impermeable micro-porous membrane or a cell-impermeable screen, respectively, in the region near the standing surface.

13 Claims, 2 Drawing Sheets

APPARATUS FOR THE CULTIVATION AND CONCENTRATION OF NON-ADHERENT CELLS AS WELL AS FOR CO-CULTIVATION OF TWO DIFFERENT CELL SPECIES

FIELD OF THE INVENTION

The present invention relates to an apparatus for the cultivation and concentration of non-adherent cells as well as for cocultivation of two different cell species which are adherent or non-adherent.

BACKGROUND OF THE INVENTION

In cell cultivation cells are introduced into culture flasks containing a nutritive medium where they grow, depending on the respective type of cell, either adherently, i.e. on the surface of the culture flask, or non-adherently, i.e. in a suspension in the nutritive medium. For harvesting and the continuing cultivation of non-adherently growing cells it has so far been common to concentrate the cells by centrifuging after the growth phase and before the further processing. There is the problem, however, that centrifuging gives rise to an undesirable aggregation of cells and to the occurrence of damage to the cells. Moreover, the manipulation involves a high risk of contamination by bacteria and fungi.

In the technique of co-culturing two cell species so far common mobile inserts are used which are equipped with a liquid-permeable but not cell-permeable membrane, which are placed into culture dishes for separating them into two cell compartments. The known inserts in culture disks, however, permit only the co-cultivation of two cell species only at a small scale and with different conditions only because one cell species is in the tissue culture dish whilst the other one is placed on the membrane. It is moreover inexpedient that the exchange of the culturing medium, the collection of the excess culture quantity and the repeated adjustment of the cell concentration is not possible or possible only within narrow limits.

From the document WO 96/00780 a cell culture apparatus subdivided into compartments is known wherein the cell compartment is defined by a lower gas-permeable membrane and by an upper membrane permeable to the nutritive medium so as to allow for a better supply of the cells with a simultaneous concentration of the macromolecular cell products in the cell compartment. Even though this cell culture apparatus allows for an exchange of the cell culture medium without centrifugation it does not permit harvesting of the macromolecular cell products without a subsequent separation of the cells by centrifuging. Apart therefrom, a co-culture of two cell species is not possible with such an apparatus.

SUMMARY OF THE INVENTION

The present invention is now based on the problem of providing an apparatus of the general type outlined above, which presents a simple structure and which serves to allow for cell production without centrifuging at a reduced risk of contamination and moreover a simple adjustment of the cell concentration.

In accordance with the present invention this problem is solved by the features defined in Patent claim 1. Preferred features which ensure-an expedient improvement of the invention are disclosed in the dependent patent claims.

On account of the inventive design of the apparatus with a fixedly mounted partial partitioning wall a partial two-chamber system is made available in an expedient manner, wherein by the time of harvesting the free excess volume of cells may expediently flow through the membrane to the other side of the chamber and the desired quantity of excess cell volume may be removed, whereupon new medium can be supplied. Whilst in culturing operation the partitioning wall is preferably located above the cell suspension as a result of the arrangement of the hollow vessel it is thus possible, without centrifugation after vertical positioning of the hollow vessel, not only to exchange the culture medium but also to adjust the cell concentration and to collect the excess culture volume. With these provisions a cell aggregation and damage to the cells are largely avoided and the adjustment of the cell concentration is facilitated by controlled exchange of the culture medium. Moreover there are less manipulations on the cell culture so that the contamination risk will be reduced.

Owing to its design and structure, the inventive apparatus is suitable for the culture of high cell concentrations with frequent and simple exchange of the medium whilst it enables the co-culture of high numbers of cells of two species under definitely identical culture conditions in the vertical orientation.

Not only the careful treatment of the cells by omission of the forces of gravitation, which are due to the centrifuging operation, but also the fact that a cell-free excess culture volume is easier to harvest than it were with the conventional centrifuging and subsequent filtering operations must be deemed to involve a special advantage of the invention. Apart therefrom, there is no loss of cells or only a loss smaller than with centrifuging and subsequent exhaustion or decanting of the excess culture medium when the inventive apparatus is employed.

It is moreover expedient that the manipulations are comparatively simpler than in prior art. For instance, the exchange of the media by conventional centrifuging takes approximately 12 minutes whereas the inventive apparatus reduces this time to roughly four minutes, especially because the manipulation is restricted to a simple tilting operation for tilting the hollow vessel from the resting surface to the surface on which it stands upright.

Another advantageous aspect is the avoidance or reduction of cell aggregation which may occur in the cell pellet during the centrifuging operation. Moreover, there is only an expediently low risk of contamination due to the reduced scope of manipulations.

Another advantage resides in the fact that due to the use of the apparatus the cluttering of a high cell concentration with frequent and simple exchange of the medium becomes possible. Moreover, there is the opportunity of permanent exchange of the medium, for instance in the production of antibodies or in the large-scale expansion of cells. Furthermore the possibility of co-culturing two different cell species is expedient, e.g. for studies into their humoral interaction.

As far as the design of the inventive apparatus is concerned it is expedient for the function and the manufacture that the passage is closed by a micro-porous membrane or a cell-impermeable screen flush with the partitioning wall, or presents a laterally projecting border or skirt. The size, shape, material, pore or mesh size of the membrane or the screen may be optionally varied in response to the respective requirements within the general framework of the desired purpose, i.e. in terms of the permeability to the medium and the excess cell volume but not to the cells. As an alternative it may also be expedient to design the entire partitioning wall—possible with the exception of a structurally required marginal plastic web—as a micro-porous membrane or cell-impermeable screen, instead of providing the at least one passage, which ensures an expedient acceleration of an exchange of the liquid in the vertical position of the hollow vessel.

The membrane which is permeable to liquids but impermeable to cells, or the screen permeable to liquids but impermeable to cells, respectively, expediently consist of a translucent material but such transparency is not definitely required whereas the hollow vessel is preferably made of a transparent material. These provisions advantageously ensure that the hollow vessel can be visually inspected in a so-called inverting microscope, i.e. with illumination from the top and with positioning of the hollow vessel above the lens so that the culture may be viewed from the bottom of the hollow vessel. The hollow vessel, and preferably the partitioning wall as well, consists of an inert transparent material, particularly even though not exclusively of polystyrene.

The height h of the partitioning wall, seen in the upright position of the hollow vessel, may expediently be so dimensioned that the cell suspension cannot flow beyond the partitioning wall into the chamber receiving the excess cell volume when the hollow vessel is in the upright position.

In cell-culturing operation the partitioning wall extends above the cell suspension and is not wetted by the latter whilst when the hollow vessel is tilted into its upright position on its supporting surface the partitioning wall ensures that the grown cell culture will be retained in that chamber section where the cells have grown while the cell-free excess volume may flow off through the membrane or the screen, respectively, to the other side of the chamber. The height h of the partitioning wall ensures in any case that this desired separation will actually be achieved.

In accordance with a preferred embodiment of the invention the volumes available on either side of the partitioning wall in the hollow vessel are approximately equal. The hollow vessel presents, in its turn, a preferably flask-shaped configuration, and in correspondence with a further expedient improvement of the invention its charging and discharging opening is oriented at an acute angle relative to the longitudinal axis of the hollow vessel in order to permit a proper access with a pipette to each chamber. In an alternative moreover provisions may be made for two such openings with a functional assignment to each chamber, instead of a single charging and discharging opening.

In a further embodiment of the invention the opening or openings is/are adapted to be loosely closed by a solid cap or a filter cap so as to ensure that a gas-tight closure will not be formed and that the circulation of gas will be possible.

BRIEF DESCRIPTION OF THE DRAWINGS

The invention will be described in the following in more details with reference to the attached drawing. In the drawing.

DETAILED DESCRIPTION OF THE PREFERRED EMBODIMENT

Figure 1:
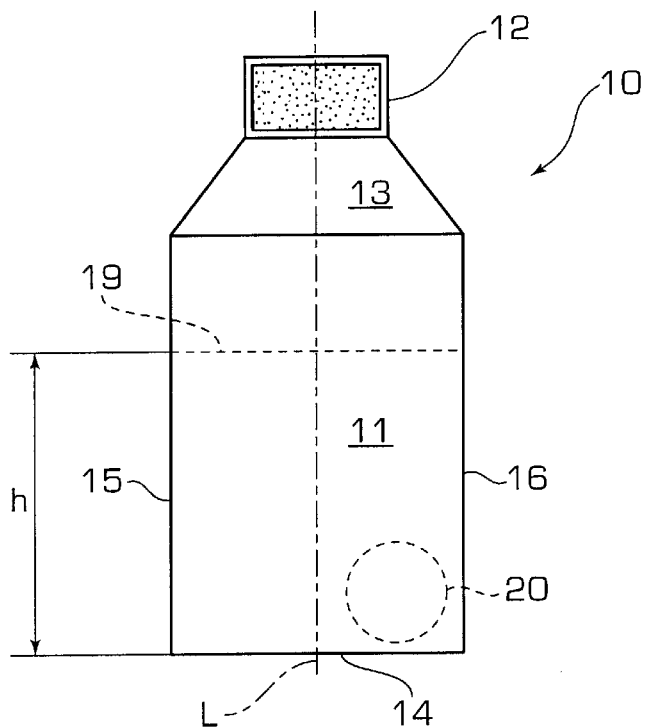
FIG. 1 is a schematic front view of a flask-shaped hollow vessel according to the invention.
Figure 2:
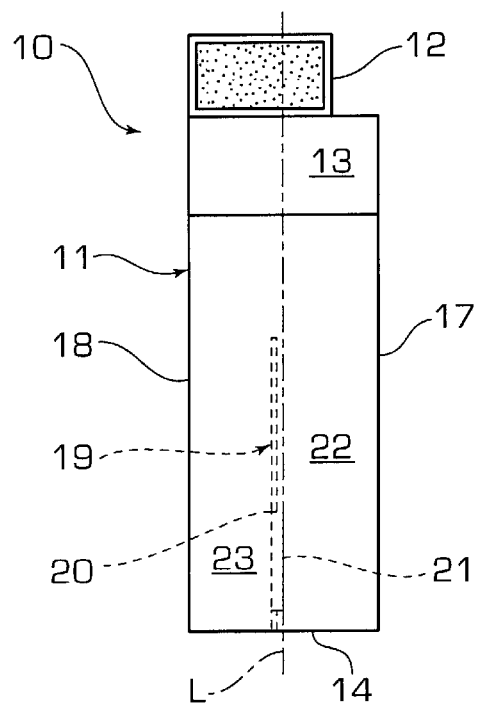
FIG. 2 is a schematic side view of the hollow vessel according to FIG. 1.

FIG. 1 is a schematic view of one embodiment of the apparatus in the form of a flask-shaped hollow vessel 10. The hollow vessel 10 comprises a parallelepiped main body 11 with a joining section 13 tapering, at an angle, towards a charging and discharging opening 12, and includes a standing surface 14 at its bottom side and short opposite lateral surfaces 15 and 16 as well as larger parallel lateral surfaces 17 and 18, as is shown in FIG. 2.

In FIG. 1 a partitioning wall 19 is indicated in dotted lines which extends from the bottom surface 14 in a direction towards the charging and discharging opening 12 in parallel with the longitudinal axis of the hollow vessel. A circular passage 20 with a liquid-permeable but cell-impermeable membrane filter 21 is provided in the partitioning wall in the vicinity of the bottom surface 14.

Figure 3:
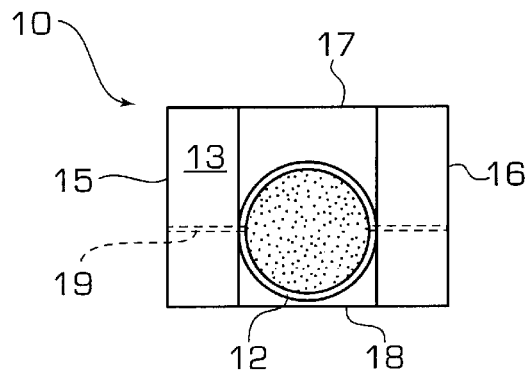
FIG. 3 is a schematic plan view of the hollow vessel according to FIG. 1.

In the illustrated embodiment the partitioning wall 19 rises upward beyond half of the height of the hollow vessel, from the bottom wall 14 to a height h, ensuring the formation of a partial two-chamber system consisting of a receiving chamber 22 for a cell suspension and a receiving chamber 23 for the excess cell volume. The charging and discharging opening 12 is arranged with an offset relative to a longitudinal axis L of the hollow vessel, as may also be seen with reference with FIG. 3.

Figure 4:
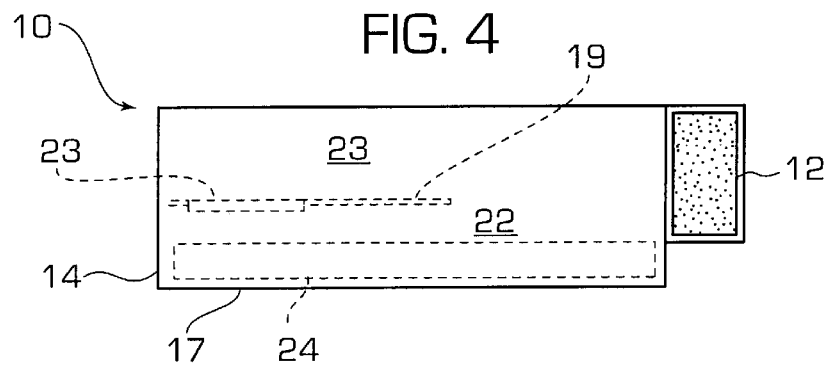
FIG. 4 is a schematic illustration of the hollow vessel according to FIG. 1, however in a horizontal position for cell culturing operation.

FIG. 4 shows the apparatus 10 in a position in which it rests on its lateral surface 17 for cell culture operation, with the chamber 22 being located underneath the chamber 23 and with the partitioning wall 19 extending in parallel with the bottom surface 17. The chamber 22 is partly filled with a cell suspension 24 consisting of a nutritive medium with cells.

Figure 5:
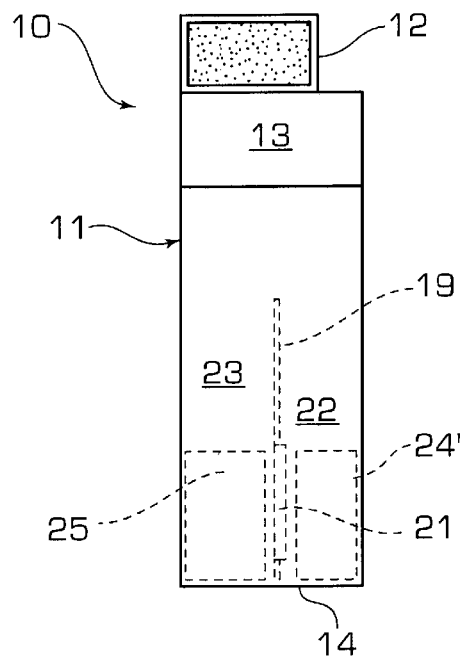
FIG. 5 is a schematic illustration of the hollow vessel in the upright position for cell harvesting operation.

In the cell-harvesting position, which is illustrated in FIG. 5, the hollow vessel 10 is placed upright on its standing surface 14. In this position a cell concentrate 24' is present in the chamber 22, which has been formed by cell growth, whilst an excess volume 25 of the culture medium has flown through the membrane 21 into the chamber 23 for separation. The chambers 22 and 23 can now be discharged with a pipette.

In the harvesting position illustrated in FIG. 5 the apparatus 10 is also suitable for the co-culture of two cell species.

What is claimed is:

1. An apparatus for the cultivation and concentration of non-adherent cells as well as for the co-culture of two different cell species, consisting of an elongate hollow vessel comprising a resting surface extending in parallel with the longitudinal axis of said vessel for positioning said hollow vessel for cell culture operation, a standing surface provided orthogonally on said longitudinal axis for positioning said hollow vessel for cell-harvesting operation or for the co-culture of two cell species, at least one closable charging and discharging opening formed on said hollow vessel on the section of the latter which is opposite to said standing surface, and a partitioning wall extending inside said hollow vessel from said standing surface, which partly subdivides the interior space of said vessel, with said partitioning wall being formed at least in parts with a liquid-permeable, however cell-impermeable membrane or a cell-impermeable screen, respectively, in the region near said standing surface.

2. An apparatus according to claim 1, wherein said membrane or said cell-impermeable screen, respectively, is flush with said partitioning wall.

3. An apparatus according to claim 1, wherein said section of said partitioning wall is configured as passage having a laterally projecting skirt.

4. An apparatus according to claim 3, wherein said passage has a circular shape.

5. An apparatus according to claim 1, wherein said membrane or said cell-impermeable screen, respectively, consists of PE or polycarbonate material.

6. An apparatus according to claim 1, wherein said hollow vessel consists of a transparent material.

7. An apparatus according to claim 6, wherein said partitioning wall consists of a translucent, preferably transparent, material.

8. An apparatus according to claim 1, wherein when said hollow vessel is in its upright position the height of said partitioning wall is so dimensioned that in this position the cell suspension will be prevented from overflowing.

9. An apparatus according to claim 1, wherein said charging and discharging opening is adapted to be loosely closed by a solid cap or a gas-permeable filter cap.

10. An apparatus according to claim 1, wherein said charging and discharging opening is oriented at an acute angle relative to the longitudinal axis of said hollow vessel.

11. An apparatus according to claim 1, wherein said charging and discharging opening is disposed at an offset relative to the longitudinal axis of said hollow vessel.

12. An apparatus according to claim 1, wherein the volumes of said chambers, which is available on either side of said partitioning wall in said hollow vessel, are approximately identical.

13. An apparatus according to claim 1, wherein said hollow vessel has a flask-shaped configuration.

* * * * *